United States Patent
Padilla-Acevedo

(10) Patent No.: US 10,975,012 B2
(45) Date of Patent: Apr. 13, 2021

(54) SYNTHESIS OF CYCLIC ORGANIC COMPOUNDS

(71) Applicant: Univation Technologies, LLC, Houston, TX (US)

(72) Inventor: Angela I. Padilla-Acevedo, Lake Jackson, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 16/650,910

(22) PCT Filed: Sep. 19, 2018

(86) PCT No.: PCT/US2018/051647
§ 371 (c)(1),
(2) Date: Mar. 26, 2020

(87) PCT Pub. No.: WO2019/067276
PCT Pub. Date: Apr. 4, 2019

(65) Prior Publication Data
US 2020/0290942 A1  Sep. 17, 2020

Related U.S. Application Data

(60) Provisional application No. 62/564,329, filed on Sep. 28, 2017.

(51) Int. Cl.
*C07C 45/45* (2006.01)
*C07C 49/633* (2006.01)

(52) U.S. Cl.
CPC ............ *C07C 45/45* (2013.01); *C07C 49/633* (2013.01); *C07C 2602/24* (2017.05)

(58) Field of Classification Search
CPC .............................. C07C 45/45; C07C 45/455
See application file for complete search history.

(56) References Cited

PUBLICATIONS

International Preliminary Report on Patentability for related PCT Application PCT/US2018/051647, dated Apr. 9, 2020 (8 pgs).
International Search Report & Written Opinion for related PCT Application PCT/US2018/051647, dated Nov. 21, 2018 (15 pgs).

Rand, et al., "Competitive Carbonium Ion Processes. Catalysis of Acylation and Acetoxylation Reactions by Polyphosphoric Acid", Journal of Organic Chemistry, vol. 31, No. 12, Dec. 1966 (6 pgs).
Schostarez, et al., "Highly Sterocontrolled Synthesis of [3.3.3] Propellane Sesquiterpenes ( )-Modhephene and ( )-Epimodhephene" Tetrahedron, vol. 37, No. 25, 1981 (6 pgs).
Tabatabaeian, et al., "Synthesis and Spectroscopic Studies of New Substitued Dinuclear (eta)5-4,5,6,7-Tetrahydroindenyl Ruthenium Complexes", Russian Journal of Coordination Chemistry, vol. 29, No. 7, 2003 (4 pgs).
Austin, et al., "Synthesis and Properties of Novel Substituted 4,5,6,7-Tetrahydroindenes and Selected Metal Complexes", Journal of Organometallic Chemistry, vol. 491, No. 1, Apr. 5, 1995 (6 pgs).
Eaton, et al., "Phosphorus Pentoxide-Methanesulfonic Acid. Conventient Alternative to Polyphosphoric Acid", Journal of Organic Chemistry, vol. 38, No. 23, Nov. 1, 1973 (4 pgs).
Daneshfar, et al., "Cellulose Sulfonic Acid as a Green, Efficient, and Reusable Catalyst for Nazarov Cyclization of Unactivated Dienones and Pyrazoline Synthesis", RSC Advances, vol. 5, No. 127, 2015 (14 pgs).
Prakash, et al., "Superacidic Trifluoromethanesulfonic Acid-induced Cycli-Acyalkylation of Aromatics", Catalysis Letters, Apr. 1, 2003 (4 pgs).
Suzuki, et al., "Superacid-Catalyzed Electrocyclization of 1-Phenyl-2-Propen-1-ones to 1-Indanones. Kinetic and Theoretical Studies of Electrocyclization of Oxonium-Carbenium Dications", Journal of the American Chemical Society, vol. 119, No. 29, 1997 (8 pgs).

*Primary Examiner* — Sikarl A Witherspoon
(74) *Attorney, Agent, or Firm* — Brooks, Cameron & Huebsch, PLLC

(57) ABSTRACT

A method comprising synthesizing a cyclic organic compound (3) via reaction of an substituted alkene (1) with an unsubstituted or substituted acrylic acid (2) in the presence of a sulfonic acid reagent to make the cyclic organic compound (3) R1(H)C=C(H)R2 (1)

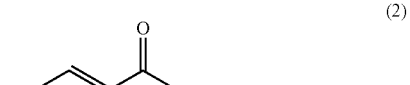

(2)

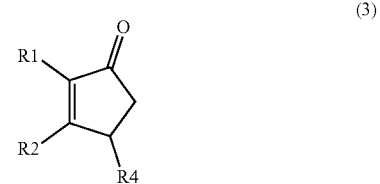

(3)

9 Claims, 2 Drawing Sheets

SYNTHESIS OF CYCLIC ORGANIC COMPOUNDS

This application is a National Stage Application under 35 U.S.C. § 371 of International Application Number PCT/US2018/051647, filed Sep. 19, 2018 and published as WO 2019/067276 on Apr. 4, 2019, which claims the benefit to U.S. Provisional Application 62/564,329, filed Sep. 28, 2017, the entire contents of which are incorporated herein by reference in its entirety.

FIELD

The field includes a method of synthesizing cyclic organic compounds.

BACKGROUND

Cyclic organic compounds are used for a wide variety of purposes, including the preparation of olefin polymerization catalysts, herbicides and pharmaceuticals. One known method of doing a cyclization reaction to make cyclic organic compounds employs polyphosphoric acid (PPA) as a reagent. For instance, see Example 105 of U.S. Pat. No. 5,721,185, in which cyclohexene is said to be reacted with crotonic acid in the presence of PPA.

See also the following. Tabatabaenian, K.; Mamaghani, M.; Neshat, A.; Masjedi, M. Synthesis and Spectroscopic Studies of New Substituted Dinuclear $\eta^5$-4,5,6,7-Tetrahydroindenyl Ruthenium Complexes. *Russian Journal of Coordination Chemistry.* 2003, 29, 7, 501. Austin, R. N.; Clark, T. J.; Dickson, T. E.; Killian, C. M.; Nile, T. A.; Shabacker, D. J.; McPhail, T. A. Synthesis and Properties of Novel Substituted 4,5,6,7-tetrahydroindenes and Selected Metal Complexes. *Journal of Organometallic Chemistry.* 1995, 491, 11. Conia, J. M.; Leriverend, M. L. *Tetrahedron Letters.* 1968, 17. 2101 (Conia et al.). L. Rand and R. J. Dolinski, *J. Org. Chem.,* 1966, 31, 3063 and L. Rand and R. J. Dolinski, *J. Org. Chem.,* 1966, 31, 4061 (collectively "Rand and Dolinski"). Yokota, K.; Kohsaka, T.; Ito, K.; Ishihara, N. Consideration of Mechanism of Styrene/Ethylene Copolymerization with Half-Titanocene Catalysts. *Journal of Polymer Science.* 2005, 43, 5041. JP10316694A to Tetsuya, I., et. al. Brancaccio G.; Lettieri, G.; Monforte, P.; Larizza, A. Farmaco, *Edizione Scientifica.* 1983, 9, 702-8. Eaton, P. E.; Carlson, G. R.; Lee, J. T. Phosphorus Pentoxide-Methanesulfonic Acid. A Convenient Alternative to Polyphosphoric Acid. *J. Org. Chem.* 1978, 38, 4071. Paquette, L. A.; Stevens, K. E., *Can. J. Chem.* 1984, 62, 2415. Paquette, L. A.; Cheney, D. L., *J. Org. Chem.* 1989, 54, 3334. *J. Org. Chem.* 1966, 3065.

Conia, et al. reported that reacting cyclohexene and crotonic acid in presence of polyphosphoric acid (PPA) exclusively gave as a sole product 2,3,4,5,6,7-hexahydro-3-methyl-1H-inden-1-one (structure 1 in Conia et al.). Conia et al. reported reacting cyclopentyl crotonate or cyclohexyl crotonate in the presence of PPA gave 3-methyl-bicyclo[3.3.0]-2-octen-1-one (40% yield, Table 1 in Conia et al.) or 2,3,4,5,6,7-hexahydro-3-methyl-1H-inden-1-one (60% yield, Table 2 in Conia et al.), respectively.

Rand and Dolinski report that using polyphosphoric acid (PPA) or a mixture of phosphorous pentoxide ($P_2O_5$ or $P_4O_{10}$) and PPA to catalyze the reaction of a cycloheptene, cyclohexene, or cyclopentene with an alpha, beta-unsaturated carboxylic acid such as acrylic acid or crotonic acid gives a reaction mixture that contains or is free of an ester by-product such as cycloheptyl crotonate, cyclohexyl crotonate, or cyclopentyl crotonate. Relatively how much of the ester by-product is made is said to depend on the amount of phosphorous pentoxide used in the mixture with PPA or the amount of the PPA or $P_2O_5$/PPA mixture relative to the amount of cycloalkene.

SUMMARY

We discovered an alternative and improved method for synthesizing a cyclic organic compound. A method for synthesizing a cyclic organic compound, the method comprising (A) contacting a compound of formula (1) ("compound (1)"): R1(H)C═C(H)R2 (1), wherein each R1 and R2 is independently H or ($C_1$-$C_6$) alkyl or substituted ($C_1$-$C_6$) alkyl, or the R1 and R2 are bonded together as —R—R— to form a ($C_1$-$C_4$) alkylene or substituted alkylene, with a compound of formula (2) ("compound (2)"):

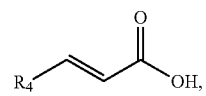

wherein R4 is H or (C1-C4)alkyl, in the presence of an effective amount of a sulfonic acid reagent and under reaction conditions sufficient to make a compound of formula (3) ("compound (3)"):

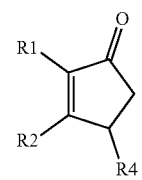

and/or its oxo/R4 regioisomer, wherein R1, R2, and R4 are as defined above.

Compound (3) prepared by the method of this disclosure may be employed in the preparation of downstream, or derivative, compounds that are useful as, e.g., olefin polymerization catalysts (e.g., post-metallocene catalysts), herbicides, and pharmaceuticals.

DETAILED DESCRIPTION

Figure 1:
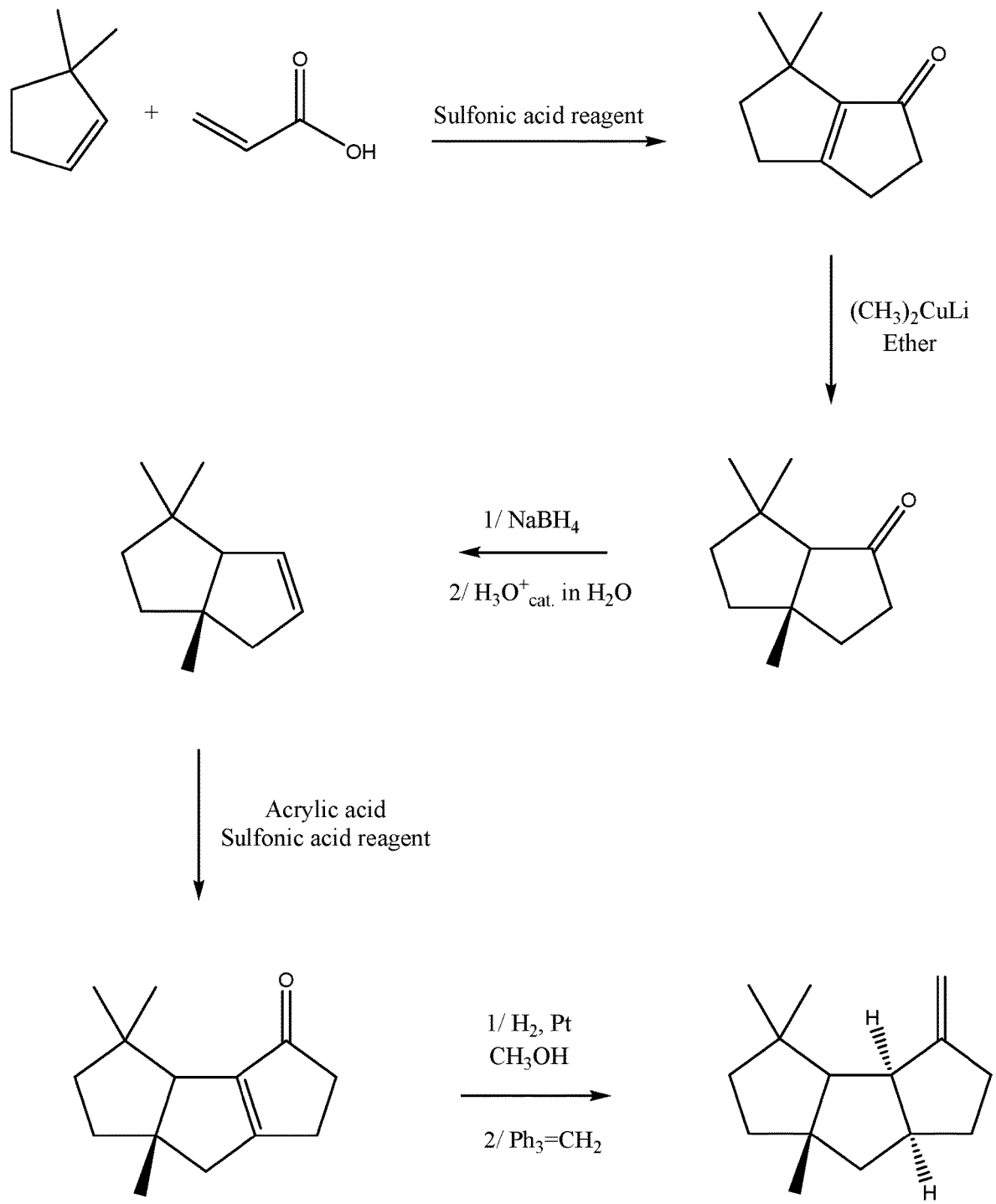
FIG. 1 shows a synthetic scheme of a prophetic synthesis of $\Delta^{9(12)}$-capnellenes.

The Summary and Abstract are incorporated here by reference.

Certain inventive embodiments are described below as numbered aspects for easy cross-referencing. Additional embodiments are described elsewhere herein.

Aspect 1. A method of synthesizing a cyclic organic compound, the method comprising (A) contacting a compound of formula (1) ("compound (1)"): R1(H)C═C(H)R2 (1), wherein each R1 and R2 is independently H or ($C_1$-$C_6$) alkyl or substituted ($C_1$-$C_6$) alkyl, or the R1 and R2 are bonded together as —R—R— to form a (C₁-C₄)alkylene, a substituted (C₁-C₄)alkylene, a (C₅-C₆)cycloalkylene, or a substituted (C₅-C₆)cycloalkylene, with a compound of formula (2) ("compound (2)"):

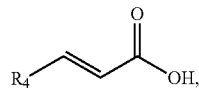
(2)

wherein R4 is H or (C1-C4)alkyl, in the presence of an effective amount of a sulfonic acid reagent under reaction conditions sufficient to make a compound of formula (3) ("compound (3)"):

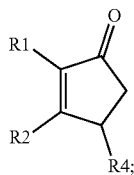
(3)

and/or its oxo/R4 regioisomer, wherein R1, R2, and R4 are as defined above.

Aspect 2. The method of aspect 1 wherein the sulfonic acid reagent comprises a (C₁-C₆)alkylsulfonic acid.

Aspect 3. The method of aspect 1 or 2 wherein the sulfonic acid reagent comprises a mixture of P₂O₅ and a (C₁-C₆)alkylsulfonic acid, or a reaction product thereof.

Aspect 4. The method of any one of the preceding aspects wherein the sulfonic acid reagent comprises a mixture of P₂O₅ and methanesulfonic acid, or a reaction product thereof.

Aspect 5. The method of any one of the preceding aspects wherein the sulfonic acid reagent comprises a mixture of 0.1 weight parts P₂O₅ and 1 weight part methanesulfonic acid, or a reaction product thereof.

Aspect 6. The method of aspect 1 or 2 wherein the sulfonic acid reagent consists essentially of methanesulfonic acid.

Aspect 7. The method of aspect 1 comprising (A) contacting a compound of formula (1a) ("compound (1a)"):

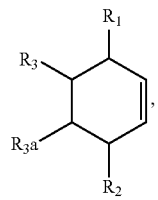
(1a)

wherein R1, R2, R3, and R3a are independently H or (C₁-C₄)alkyl, or any two adjacent R1 to R3a groups are bonded together to form a (C₁-C₄)alkylene and the remaining two R1 to R3a groups independently are H or (C₁-C₄)alkyl, with a compound of formula (2) ("compound (2)"):

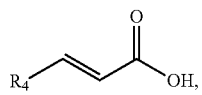
(2)

wherein R4 is H or (C₁-C₄)alkyl, in the presence of an effective amount of a sulfonic acid reagent and under reaction conditions sufficient to make a compound of formula (3a) ("compound (3a)"):

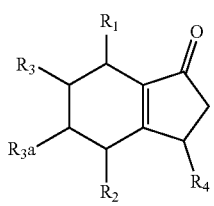
(3a)

and/or its oxo/R4 regioisomer; wherein R1 to R4 are as defined above. Compound (1a) is an embodiment of compound (1) wherein R1 and R2 are taken together to form —R—R—, wherein —R—R— is of formula —C(H)(R1)—C(H)(R3)-C(H)(R3a)-C(H)(R2)-, wherein each of R1 to R3a independently is H or (C₁-C₄)alkyl, or any two adjacent R1 to R3a groups are bonded together to form a (C₁-C₄) alkylene and the remaining two R1 to R3a groups independently are H or (C₁-C₄)alkyl. In some aspects each of R1 to R3a independently is H or (C₁-C₄)alkyl; alternatively two adjacent R1 to R3a groups are bonded together to form a (C₁-C₄)alkylene and the remaining two R1 to R3a groups independently are H or (C₁-C₄)alkyl. The "/" in "oxo/R4 regioisomer" indicates the groups that are in different positions in the oxo/R4 regioisomer relative to the compound (3a). That is, the positions of the oxo (=O) and R4 substituents are switched with each other relative to their positions in the compound (3a). Thus, in the oxo/R4 regioisomer the oxo is bonded to the carbon atom bearing R4 in compound (3a) and the R4 in the oxo/R4 regioisomer is bonded to the carbon atom bearing the oxo in compound (3a). The regioisomer relationships are illustrated by the example compounds (3a1) and (3a2):

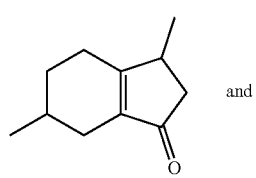
(3a1)

and

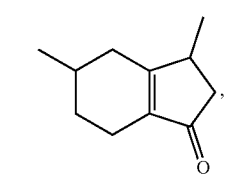
(3a2)

which are methyl/oxo regioisomers wherein compound (3a1) is a compound of formula (3a) wherein R1, R2, and R3a are H and R3 and R4 are methyl and compound (3a2) is a compound of formula (3a) wherein R1, R2, and R3 are H and R3a and R4 are methyl. This description of regioisomers applies to other applicable compounds described herein. In another embodiment 3,3-dimethyl-1-cyclohexene is used in place of the compound (1a). The 3,3-dimethyl-1-cyclohexene is a geminal-dimethyl analog of cyclohexene and is an embodiment of compound (1) wherein R1 and R2 are taken together to form —R—R— which is a 1,1-dimethyl substituted butylene. The embodiment yields an embodiment of compound (3) that is an analog of compound (3a) wherein R2, R3 and R3a are H, R1 is methyl, and the carbon atom bearing R1 is substituted with a second methyl.

Aspect 8. The method of aspect 1 comprising (A) contacting a compound of formula (1b) ("compound (1b)"):

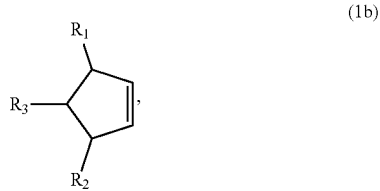

(1b)

wherein R1, R2, and R3 are independently H or (C1-C4)alkyl, or any two adjacent R1 to R3 groups are bonded together to form a $(C_1-C_4)$alkylene and the remaining one of the R1 to R3 groups is H or $(C_1-C_4)$alkyl, with a compound of formula (2) ("compound (2)"):

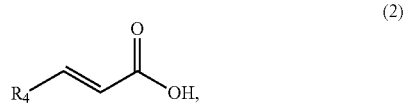

(2)

wherein R4 is H or (C1-C4)alkyl, or any two adjacent R1 to R3 groups are bonded together to form a $(C_1-C_4)$alkylene and the remaining R1 to R3 group independently is H or $(C_1-C_4)$alkyl, in the presence of an effective amount of a sulfonic acid reagent and under reaction conditions sufficient to make a compound of formula (3b) ("compound (3b)"):

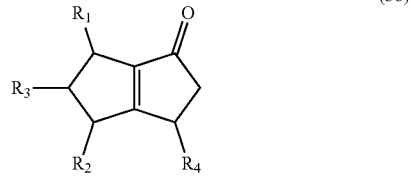

(3b)

and/or its oxo/R4 regioisomer; wherein R1 to R4 are as defined above. Compound (1b) is an embodiment of compound (1) wherein R1 and R2 are taken together to form —R—R—, wherein —R—R— is of formula —C(H)(R1)-C(H)(R3)-C(H)(R2), wherein each of R1 to R3 independently is H or $(C_1-C_4)$alkyl, or any two adjacent R1 to R3 groups are bonded together to form a $(C_1-C_4)$alkylene and the remaining one of the R1 to R3 groups is H or $(C_1-C_4)$alkyl. In some aspects each of R1 to R3 independently is H or $(C_1-C_4)$alkyl; alternatively two adjacent R1 to R3 groups are bonded together to form a $(C_1-C_4)$alkylene and the remaining one of the R1 to R3 groups is H or $(C_1-C_4)$alkyl. In another embodiment 3,3-dimethyl-1-cyclopentene is used in place of the compound (1a). The 3,3-dimethyl-1-cyclopentene is a geminal-dimethyl analog of cyclopentene and is an embodiment of compound (1) wherein R1 and R2 are taken together to form —R—R— which is a 1,1-dimethyl substituted propylene. The embodiment yields an embodiment of compound (3) that is an analog of compound (3b) wherein R2 and R3 are H, R1 is methyl, and the carbon atom bearing R1 is substituted with a second methyl.

Aspect 9. The method of aspect 1 comprising (A) contacting a compound of formula (1c) ("compound (1c)"):

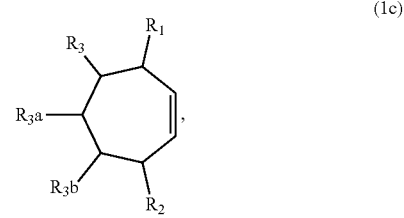

(1c)

wherein R1, R2, R3, R3a, and R3b are independently H or (C1-C4)alkyl, or any two adjacent R1 to R3b groups are bonded together to form a $(C_1-C_4)$alkylene and the remaining three R1 to R3b groups independently are H or $(C_1-C_4)$alkyl, with a compound of formula (2) ("compound (2)"):

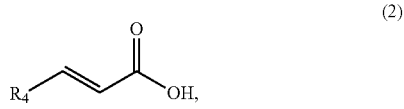

(2)

wherein R4 is H or (C1-C4)alkyl, in the presence of an effective amount of a sulfonic acid reagent and under reaction conditions sufficient to make a compound of formula (3c) ("compound (3c)"):

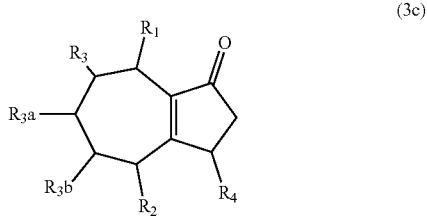

(3c)

and/or its oxo/R4 regioisomer; wherein R1 to R4 are as defined above. Compound (1c) is an embodiment of compound (1) wherein R1 and R2 are taken together to form —R—R—, wherein —R—R— is of formula —C(H)(R1)-C(H)(R3)-C(H)(R3a)-C(H)(R3b)-C(H)(R2), wherein each of R1 to R3b independently is H or $(C_1-C_4)$alkyl, or any two adjacent R1 to R3b groups are bonded together to form a $(C_1-C_4)$alkylene and the remaining three R1 to R3b groups independently are H or $(C_1-C_4)$alkyl. In some aspects each of R1 to R3b independently is H or $(C_1-C_4)$alkyl; alternatively two adjacent R1 to R3b groups are bonded together to form a $(C_1-C_4)$alkylene and the remaining three of the R1 to R3b groups independently are H or $(C_1-C_4)$alkyl. In another embodiment 3,3-dimethyl-1-cycloheptene is used in place of the compound (1c). The 3,3-dimethyl-1-cycloheptene is a geminal-dimethyl analog of cycloheptene and is an embodiment of compound (1) wherein R1 and R2 are taken together to form —R—R— which is a 1,1-dimethyl substituted pentylene. The embodiment yields an embodiment of compound (3) that is an analog of compound (3c) wherein R2, R3, R3a and R3b are H, R1 is methyl, and the carbon atom bearing R1 is substituted with a second methyl.

In some embodiments the sulfonic acid reagent is, or consists essentially of, the $P_2O_5/H_3CSO_3H$ mixture, or a reaction product thereof. Alternatively the sulfonic acid reagent may consist essentially of an alkylsulfonic acid such as a $(C_1-C_6)$alkylsulfonic acid such as methanesulfonic acid. The expression "consist essentially of the $P_2O_5/H_3CSO_3H$ mixture" means the sulfonic acid reagent and step (A) are free of PPA. The expression "consist essentially of the alkylsulfonic acid such as a $(C_1-C_6)$alkylsulfonic acid such as methanesulfonic acid" means the sulfonic acid reagent and step (A) are free of PPA and $P_2O_5$. In some aspects the $P_2O_5/H_3CSO_3H$ mixture is a 0.1/1 (weight/weight) $P_2O_5/H_3CSO_3H$ mixture, known as Eaton's reagent.

The method of the disclosure may be employed as a step in the preparation of downstream compounds, such as synthetic and/or naturally occurring products. For example, the method of the disclosure may be employed in the inventive synthesis of $\Delta^{9(12)}$-capnellenes as prophetically shown in the reaction scheme of FIG. 1. Such compounds have been isolated from the soft coral *Capnella imbricata*. These capnellenes were shown to have biologic activity; see, e.g. *Tetrahedron* 54(42), 12953-12958. In FIG. 1, a step in the synthesis employs the sulfonic acid reagent and is an example of the method of this disclosure for synthesizing a cyclic organic compound. The top right structure in FIG. 1 is an embodiment of compound (3) wherein R1 and R2 are bonded together as —R—R— to form a substituted ($C_6$) cycloalkylene that is a substituted cyclopentan-1,2-diyl, wherein the substituents are germinal dimethyl. The inventive method is applied a second time in the scheme in FIG. 1 to make the bottom left compound. The other steps in the following synthesis may be conducted according to methods well-known to those skilled in the art.

Figure 2:
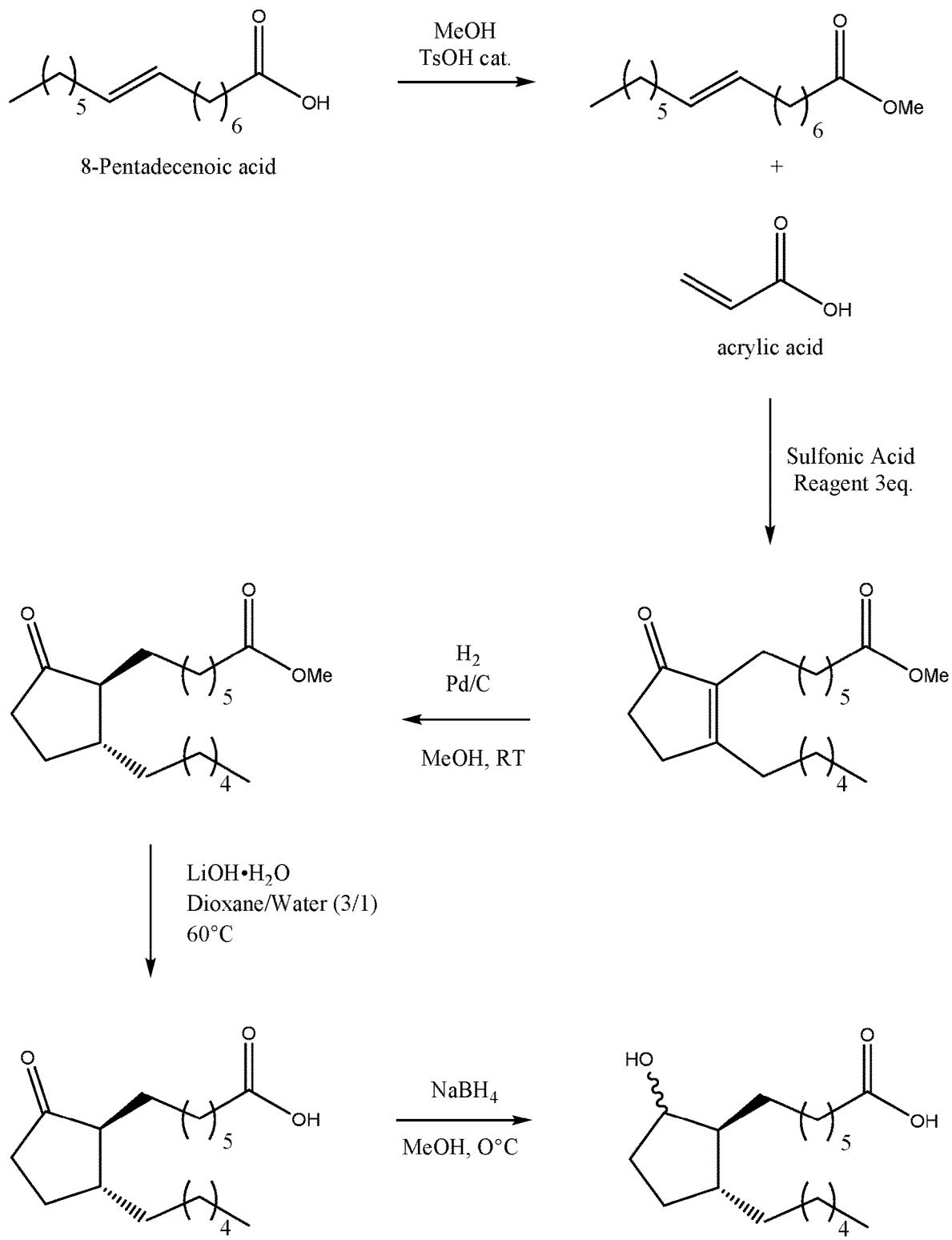
FIG. 2 shows a synthetic scheme of a prophetic synthesis of ROSAPROSTOL.

As another example, the method of the disclosure may be employed in the inventive synthesis of ROSAPROSTOL, which is a trade name for 7-(2-hexyl-5-hydroxycyclopentane)heptanoic acid, as prophetically shown in the reaction scheme of FIG. 2. The sodium salt of ROSAPROSTOL is a mixture of (1RS,2SR,5RS) and (1RS,2SR,5SR) isomers and has been launched in Italy under the name ROSAL for the treatment of gastric and duodenal ulcers. The step in in the following synthesis that employs the sulfonic acid reagent is an example of the method of this disclosure. The middle right structure in FIG. 2 is an embodiment of compound (3) wherein R1 is pentyl and R2 is an alkylcarboxylic methyl ester The other steps in the following synthesis may be conducted according to methods well-known to those skilled in the art.

The compound (1) may be cyclic or acyclic and substituted or unsubstituted. The unsubstituted cyclic embodiments of compound (1) may have at least 3 carbon atoms, alternatively from 3 to 50 carbon atoms, alternatively from 3 to 20 carbon atoms, alternatively from 3 to 8 carbon atoms. The unsubstituted acyclic embodiments of compound (1) may have at least 2 carbon atoms, alternatively from 2 to 50 carbon atoms, alternatively from 2 to 20 carbon atoms, alternatively from 2 to 8 carbon atoms. Examples of compound (1) include ethylene, propene, cyclopropene, one or more butenes, cyclobutene, one or more pentenes, cyclopentene, one or more hexenes, cyclohexene, one or more heptenes, cycloheptene, etc. Mixtures of compound (1) may be employed in the inventive method.

Examples of substituents are unsubstituted $(C_1-C_6)$alkyl halogen, $(C_1-C_6)$alkyl-carboxylic ester; alternatively $(C_1-C_6)$alkyl. The $(C_1-C_6)$alkyl-carboxylic ester may be a $(C_1-C_6)$alkyl-carboxylic methyl ester or ethyl ester. In FIG. 2 the middle right structure contains a substituent that is a hexyl and a substituent that is a $(C_1-C_6)$alkyl-carboxylic ester wherein the $(C_1-C_6)$alkyl portion is —$(CH_2)_6$ and the carboxylic ester portion is —$CO_2CH_3$.

Alkyl means an unsubstituted univalent saturated acyclic hydrocarbon that is straight chain (1 or more carbon atoms), branched chain (if 3 or more carbon atoms), or cyclic (if 3 or more carbon atoms). Each $(C_1-C_4)$alkyl is independently methyl, ethyl, propyl, 1-methylethyl, butyl, 1-methylpropyl, 2-methylpropyl, or 1,1-dimethylethyl. Alternatively each $(C_1-C_4)$alkyl is independently a $(C_1-C_3)$alkyl; alternatively a $(C_2-C_4)$alkyl; alternatively $(C_1-C_2)$alkyl; alternatively $(C_2-C_3)$alkyl; alternatively $(C_3-C_4)$alkyl; alternatively methyl or $(C_3)$alkyl. In some aspects each $(C_1-C_4)$alkyl is independently a $(C_1-C_3)$alkyl and each $(C_1-C_3)$alkyl is independently methyl, ethyl, propyl, or 1-methylethyl; alternatively methyl, propyl, or 1-methylethyl; alternatively methyl; alternatively ethyl; alternatively propyl; alternatively 1-methylethyl. Substituted alkyl is an alkyl as defined above except wherein one or more hydrogen atoms is formally replaced by a substituent such as unsubstituted alkyl, halogen, or alkylcarboxylic ester.

Alkylene means an unsubstituted divalent saturated acyclic hydrocarbon that may be straight chain (1 or more carbon atoms), branched chain (if it contains 3 or more carbon atoms), or cyclic (if it contains 3 or more carbon atoms). Each $(C_1-C_4)$alkylene is independently methylene ($CH_2$), ethylene ($CH_2CH_2$), propylene ($CH_2CH_2CH_2$), 1-methylethylene ($CH(CH_3)CH_2$), butylene ($(CH_2)_4$), 1-methylpropylene ($CH(CH_3)CH_2CH_2$), 2-methylpropylene ($CH_2CH(CH_3)CH_2$), or 1,1-dimethylethylene ($C(CH_3)_2CH_2$). Substituted alkylene is an alkylene as defined above except wherein one or more hydrogen atoms is formally replaced by a substituent such as unsubstituted alkyl, halogen, or alkylcarboxylic ester.

Cycloalkylene means an unsubstituted divalent saturated cyclic hydrocarbon that contains 5 or more carbon atoms. Each $(C_5-C_6)$cycloalkylene is independently a cyclopentylene or a cyclohexylene. Typically the cyclopentylene is a cyclopentan-1,2-diyl and the cyclohexylene is a cyclohexan-1,2-diyl. Substituted cycloalkylene is a cycloalkylene as defined above except wherein one or more hydrogen atoms is formally replaced by a substituent such as unsubstituted alkyl, halogen, or alkylcarboxylic ester.

The product of the cyclization process is the compound of formula (3) ("compound (3)"):

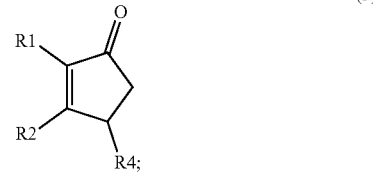

(3)

and/or its oxo/R4 regioisomer; wherein R1, R2, and R4 are as defined above. Examples of compound (3) are shown in FIGS. 1 and 2 and in the Examples later. Compound (3) may or may not contain fused rings, depending on the reactants employed in its preparation. Compound (3) may be monocyclic, bicyclic, or tricyclic. Further examples of compound (3) are described below.

Bicyclo[4.3.0]nonene compounds are molecules having a six-membered carbocyclic ring fused to a five-membered carbocyclic ring. The five-membered carbocyclic ring may contain a carbon-carbon double bond, which may be shared at the fusion point with the six-membered carbocyclic ring. Examples are compound (3a) and its oxo/R4 regioisomers, compounds (3a1) and (3a2).

Bicyclo[5.3.0]decene compounds are molecules having a seven-membered carbocyclic ring fused to a five-membered carbocyclic ring. The five-membered carbocyclic ring may contain a carbon-carbon double bond, which may be shared at the fusion point with the seven-membered carbocyclic ring. Examples are (3c) and its oxo/R4 regioisomers.

Bicyclo[3.3.0]octene compounds are molecules having a five-membered carbocyclic ring fused to a five-membered carbocyclic ring. The second five-membered carbocyclic ring may contain a carbon-carbon double bond, which may be shared at the fusion point with the first five-membered carbocyclic ring. Examples are compound (3b) and its oxo/R4 regioisomers.

In some aspects the method employs the $P_2O_5/H_3CSO_3H$ mixture and further comprises limitation (i) or (ii): (i) a step of preforming the $P_2O_5/H_3CSO_3H$ mixture before the contacting step (A) and in the absence of at least one, alternatively each of the compounds (1) to (3) and the oxo/R4 regioisomer; or (ii) wherein the contacting step (A) further comprises contacting the $P_2O_5$ and $H_3CSO_3H$ together in the presence of at least one, alternatively each of the compounds (1) and (2) to form the $P_2O_5/H_3CSO_3H$ mixture in situ.

Compound means a molecule or collection of molecules. When in compound (1) the R1 and R2 are unsubstituted and are bonded together as —R—R— to form a linear alkylene that is $(CH_2)_4$, then compound (1) is cyclohexene. When R1 and R2 groups are unsubstituted and are bonded together as —R—R— to form a branched $(C_5)$alkan-1,4-diyl or higher, then compound (1) is an alkyl substituted cyclohexene. When R4 is H, the compound (2) has CAS number 79-10-7 and is acrylic acid. When R4 is methyl, the compound (2) has CAS number 107-93-7 and is (E)-2-butenoic acid, also known as crotonic acid or (trans) 3-methylacrylic acid. Compounds (1) and (2) may be available from commercial suppliers or may be synthesized by well-known methods.

Dehydration reaction conditions include temperature and reagents effective for enhancing rate of loss of water from compound (4) and/or its (HO,R5)/R4 regioisomer. Example of such reagents are 1 Molar (M) or higher hydrochloric acid (aqueous HCl) or anhydrous HCl in an organic solvent such as ethanol, tetrahydrofuran or toluene. The hydrochloric acid may be from 1 M to 8 M, alternatively from 2 M to 6 M.

Effective amount is a quantity sufficient for enabling the making of a detectable amount of intended product. An effective amount of the sulfonic acid reagent is a quantity thereof sufficient for enabling the making of a detectable amount of compound (3) and/or its oxo/R4 regioisomer. Detectable amounts may be characterized by any suitable analytical method such as 1H-nuclear magnetic resonance (1H-NMR), high performance liquid chromatography (HPLC, versus a known standard), gas chromatography (GC, versus a known standard), or mass spectrometry; typically 1H-NMR. The effective amount of the sulfonic acid reagent used in step (A) may vary depending upon its composition, reaction conditions, and costs. A skilled person may determine an optimal effective amount thereof by starting with an initial reaction mixture of (1), (2), and 95 wt % of the sulfonic acid reagent, and thereafter systematically try reaction mixtures containing lower wt % of the sulfonic acid reagent until an optimal result under the reaction conditions is found. When the sulfonic acid reagent is the $P_2O_5/H_3CSO_3H$ mixture, the effective amount may be from 50 to 95 wt %, alternatively from 50 to 80 wt % based on total weight of (1), (2), and the sulfonic acid reagent. Alternatively, the effective amount of the a $P_2O_5/H_3CSO_3H$ mixture may be from 1 to 10 mole equivalents, alternatively 1 to 5 mole equivalents, alternatively 1 to 3 mole equivalents thereof relative to the number of moles of compound (1). For example, if 1.0 mole of compound (1) is used in the contacting step (A), then the effective amount of the $P_2O_5/H_3CSO_3H$ mixture may be from 1 to 10 moles, alternatively 1 to 5 moles, alternatively 1 to 3 moles.

Hydride-functional reducing agent means a compound having a metal-H bond capable of adding to an oxo group of a ketone to give a tertiary alcohol. Suitable metals include Al and B. Suitable hydride-functional reducing agents are lithium aluminum hydride ($LiAlH_4$), diisobutyl aluminum hydride ($Bu_2AlH$), and sodium borohydride ($NaBH_4$).

Methanesulfonic acid is a compound of formula $H_3CSO_3H$ and has CAS number 75-75-2 and is widely available from commercial suppliers.

Mixture of a phosphorous pentoxide and methanesulfonic acid or $P_2O_5/H_3CSO_3H$ mixture is a blend or reaction product of phosphorous pentoxide and methane sulfonic acid. The weight/weight ratio of $P_2O_5/H_3CSO_3H$ in the mixture may be from 0.1 to 1 alternatively 0.15 to 1, alternatively 0.2 to 1. The 0.1/1 (wt/wt) $P_2O_5/H_3CSO_3H$ mixture is commercially available and, again, may be referred to as Eaton's reagent. The mixture of $P_2O_5$ and $CH_3SO_3H$ may be formed in situ in the presence of the compound (1) and/or (2), such as prior to or during the contacting step (A). Alternatively, the mixture of $P_2O_5$ and $CH_3SO_3H$ may be preformed before contacting step (A). It is convenient to preform the $P_2O_5/CH_3SO_3H$ mixture before contacting step (A), and store the resulting preformed mixture for later use in embodiments of the contacting step (A). In some aspects the method further comprises limitation (i) or (ii): (i) a step of preforming the $P_2O_5/H_3CSO_3H$ mixture before the contacting step (A) and in the absence of at least one, alternatively each of the compounds (1) and (2); or (ii) wherein the contacting step further comprises contacting a phosphorous pentoxide and methanesulfonic acid together in the presence of at least one, alternatively each of the compounds (1) and (2) to form the $P_2O_5/H_3CSO_3H$ mixture in situ.

A sulfonic acid reagent is an acidic material having O—P(O)—OH acid groups and/or C—S(O)$_2$—OH acid groups, or an acidic reaction product thereof. The sulfonic acid reagent may be, or may consist essentially of, a mixture of a phosphorous pentoxide and methanesulfonic acid ("$P_2O_5/H_3CSO_3H$ mixture"), or a reaction product thereof. In some embodiments the sulfonic acid reagent consists essentially of the $P_2O_5/H_3CSO_3H$ mixture. Alternatively the sulfonic acid reagent may consist essentially of an alkylsulfonic acid such as a $(C_1-C_6)$alkylsulfonic acid such as methanesulfonic acid. The expression "consist essentially of" means the phosphoric and/or sulfonic acid reagent and step (A) are free of PPA.

Polyphosphoric acid or PPA has CAS no. 8017-16-1 and is a compound generally of formula HO—[P(=O)(OH)]$_n$—H, wherein subscript n indicates degree of polymerization.

Phosphorous pentoxide is a compound of formula $P_2O_5$ and has CAS number 1314-56-3 and is widely available from commercial suppliers.

In some aspects each reactant, reagent, solvent, or other material used in the inventive methods, and each product thereof, is free of Pt, Ni, Pd, Rh, and Ru.

Included in the term "under reaction conditions sufficient to make" are reaction temperature; reaction pressure; reaction atmosphere; reaction solvent, if any; reactant and reagent concentrations; molar ratios of reactants to each other and to reagents; and absence of negating compounds. Reaction pressure is typically ambient pressure (e.g., 101 kilopascals (kPa). If desired, reactions may be carried out in a fume hood under an anhydrous molecular nitrogen gas atmosphere or using Schlenck line techniques and conditions.

Reaction temperatures under reaction conditions sufficient to make may vary. In step (A) when using the $P_2O_5/H_3CSO_3H$ mixture the reaction temperature may be from −78° C. to 30° C., alternatively from −30° to 25° C., alternatively from 0° to 25° C.

The use or not of solvent and the type of solvent if used under reaction conditions sufficient to make may vary from step to step. Step (A) may be free of solvent or advantageously may employ a solvent. When the sulfonic acid reagent is the $P_2O_5/H_3CSO_3H$ mixture, a polar aprotic solvent may be employed. The polar aprotic solvent may be selected from sulfolane, 1,2-dimethoxyethane, 1-methoxy-2-(2-methoxyethoxy)ethane, and mixtures of any two or more thereof. The amount of polar aprotic solvent employed is not particularly important. The foregoing polar aprotic solvents may serve to solubilize the compounds (1) and (2) and/or the $P_2O_5/H_3CSO_3H$ mixture. The amount of solvent employed may be sufficient to prepare a starting solution of that is from 0.5 Molar (M) to 5 M, or 1 M to 2.5 M of $P_2O_5/H_3CSO_3H$ mixture in the compound (2). The polar aprotic solvent may allow the contacting step (A) to be performed at lower temperatures within the ranges given above therefor. A polar aprotic solvent is used for the $P_2O_5/H_3CSO_3H$ mixture because a protic solvent is expected to undesirably react with the $P_2O_5/H_3CSO_3H$ mixture, which is a powerful dehydrating agent. The polar aprotic solvent may be of intermediate polarity in order to co-solubilize the compounds (1) and (2) and $P_2O_5/H_3CSO_3H$ mixture. The polar aprotic solvent may be capable of producing a homogeneous solution of the compounds (1) and (2) at 25° C., alternatively at 10° C., alternatively at 0° C. A homogeneous solution is not required for successful reaction of compounds (1) and (2) in the presence of the sulfonic acid reagent.

Reaction atmosphere included under reaction conditions sufficient to make may be anhydrous molecular nitrogen gas or Schlenck line conditions for step (A) (cyclocondensation).

Reaction concentrations of reactants and reagents included under reaction conditions sufficient to make may be independently in the range from 0.1 to 1.4 M, alternatively 0.25 to 1 Molar (M), alternatively 0.4 to 1 M.

Molar ratios of reactants to each other and to reagents included under reaction conditions sufficient to make may vary from 0.25 times to 1.5 times theoretical reaction stoichiometry, alternatively from 0.99 times to 1.2 times theoretical reaction stoichiometry, alternatively from 1.0 to 1.1 times theoretical reaction stoichiometry, depending upon the reactants and reagents used. In step (A) (cyclocondensation) the theoretical reaction stoichiometry of compound (1) to compound (2) is 1.0 to 1.0.

In some aspects the method further comprises a separation step, the separation step comprising separating the cyclic organic compound, e.g. compound (3a), from its oxo/R4 regioisomer to give a purified compound (3a) and/or a purified regioisomer thereof, e.g. oxo/R4. The separation step may comprise one or more of fractional distillation, fractional crystallization, or chromatography such as gas chromatography or liquid chromatography such as, for example, ambient pressure, medium pressure or high pressure liquid chromatography on a silica gel column using one or more organic solvents as eluent.

Negating agents should not be included under reaction conditions sufficient to make. In step (A) (cyclocondensation), a negating agent may be a quantify of a basic compound that would neutralize the acidity of the sulfonic acid reagent or otherwise render it ineffective; or a negating agent may be an unsaturated aliphatic compound that would react with compound (2) before compound (2) could react with compound (1).

A compound includes all its isotopes and natural abundance and isotopically-enriched forms. The enriched forms may have medical or anti-counterfeiting uses.

In some aspects any compound, composition, formulation, mixture, or reaction product herein may be free of any one of the chemical elements selected from the group consisting of: H, Li, Be, B, C, N, O, F, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Tc, Ru, Rh, Pd, Ag, Cd, In, Sn, Sb, Te, I, Cs, Ba, Hf, Ta, W, Re, Os, Ir, Pt, Au, Hg, Tl, Pb, Bi, lanthanoids, and actinoids; with the proviso that chemical elements required by the compound, composition, formulation, mixture, or reaction product (e.g., C and H required by a polyolefin or C, H, and O required by an alcohol) are not excluded.

The following apply unless indicated otherwise. Alternatively precedes a distinct embodiment. ASTM means the standards organization, ASTM International, West Conshohocken, Pa., USA. ISO means the standards organization, International Organization for Standardization, Geneva, Switzerland. Any comparative example is used for illustration purposes only and shall not be prior art. Free of or lacks means a complete absence of; alternatively not detectable. IUPAC is International Union of Pure and Applied Chemistry (IUPAC Secretariat, Research Triangle Park, N.C., USA). May confers a permitted choice, not an imperative. Operative means functionally capable or effective. Optional (ly) means is absent (or excluded), alternatively is present (or included). PPM are weight based. Properties are measured using a standard test method and conditions for the measuring (e.g., viscosity: 23° C. and 101.3 kPa). Ranges include endpoints, subranges, and whole and/or fractional values subsumed therein, except a range of integers does not include fractional values. Room temperature: 23° C.±1° C. Substituted when referring to a compound means having, in place of hydrogen, one or more substituents, up to and including per substitution.

EXAMPLES

Unless noted otherwise herein, use the following preparations for characterizations. Carry out syntheses under an atmosphere of dry nitrogen in a glovebox when indicated. Perform reactions requiring anhydrous conditions under an atmosphere of dry nitrogen in oven-dried glassware cooled under a stream of dry nitrogen. Anhydrous toluene, hexanes, tetrahydrofuran, diethyl ether and 1,2-dimethoxyethane are from Sigma-Aldrich. Solvents that are used for experiments performed in a nitrogen-filled glovebox are further dried by storage over activated 4 Angstrom (Å) molecular sieves. All other reagents are purchased from Sigma-Aldrich and are used as received. For example, $P_2O_5/CH_3SO_3H$ (0.1/1 wt/wt) mixture may be purchased from Sigma-Aldrich (CAS #: 39394-84-8).

$^1$H-NMR (proton nuclear magnetic resonance spectroscopy) chemical shift data are reported in parts per million (ppm) down field relative to tetramethylsilane (TMS), δ scale, using residual protons in deuterated solvent as references. The $^1$H-NMR chemical shift data measured in $CDCl_3$ are referenced to 7.26 ppm, data measured in benzene-d6 ($C_6D_6$) to 7.16 ppm, data measured in tetrahydrofuran-d8 (THF-d8) to 3.58 ppm. $^1$H-NMR chemical shift data are reported in the format: chemical shift in ppm (multiplicity, coupling constant(s) in Hertz (Hz), and integration value. Multiplicities are abbreviated s (singlet), d (doublet), t (triplet), q (quartet), pent (pentet), m (multiplet), and br (broad).

Inventive Example 1: synthesis of compound (3a-1) using $P_2O_5/H_3CSO_3H$ mixture: compound (3a) wherein R1 to R3a is H and R4 is methyl. Under a nitrogen atmosphere in a 250 mL round bottom flask equipped with a stir bar, add (E)-2-butenoic acid (compound (2) wherein R4 is methyl, 10 g, 116 mmol), then add cyclohexene (compound (1a) wherein R1 to R3a is H, 9.6 mL, 116 mmol). Cool the reaction mixture to 0° C. Next, add dropwise $P_2O_5/H_3CSO_3H$ mixture (0.1/1) (55.3 mL, 348 mmol) at 0° C. Warm up the reaction mixture with stirring to ambient temperature, and then continue stirring for 20 hours. Dilute the resulting crude product with 50 mL of water. Add solid $NaHCO_3$ until bubbling subsides and pH of the reaction mixture reaches pH 8 to pH 9. Separate the aqueous and organic layers in a separatory funnel. Extract the aqueous layer three times with diethyl ether (3×50 mL). Combine the organic layers, and wash with brine (50 mL). Dry over magnesium sulfate and filter. Remove the solvent in vacuo to give 13.1 g compound (3-1) as a dark brown liquid product (75% yield). Purify the compound (3a-1) by distillation at reduced pressure (b.p. 75-80° C./1.75 mm Hg) to give compound (3a-1) as a colorless liquid. $^1$H-NMR (400 MHz, $CDCl_3$) δ 2.79-2.65 (m, 1H), 2.60 (ddt, 1H), 2.48-2.32 (m, 1H), 2.22-2.02 (m, 3H), 2.02-1.88 (m, 1H), 1.82-1.44 (m, 4H), 1.14 (d, 3H).

Inventive Example 2: synthesis of compound (3a-2) and its oxo/R4 regioisomer using $P_2O_5/H_3CSO_3H$ mixture: compound (3a) wherein R1, R2, and R3a is H and R3 and R4 are methyl, and its oxo/R4 regioisomer. Under a nitrogen atmosphere, in a round bottom flask equipped with a stir bar, add (E)-2-butenoic acid (compound (2) wherein R4 is methyl, 1 g, 11.6 mmol) followed by 4-methyl-1-cyclohexene (compound (1a) wherein R3 is methyl, 1.4 mL, 11.6 mmol). Next, add 1,2-dimethoxyethane (5.5 mL). Cool the reaction mixture to −20° C. Next, add dropwise a $P_2O_5/H_3CSO_3H$ mixture (0.1:1) (5.53 mL, 34.8 mmol) at −20° C. Warm up the reaction mixture with stirring to ambient temperature, and then continue stirring for 20 hours. Dilute the mixture into 50 mL of water and 50 mL of diethyl ether. Add solid NaHCO3 until bubbling subsides. Decant the liquid layer, and separate the aqueous and organic layers. Extract the aqueous layer twice with diethyl ether (2×15 mL). Combine the combined organic layers, and wash with saturated $NaHCO_3$ (20 mL), then with brine (30 mL). Dry over magnesium sulfate and filter. Remove the solvent in vacuo to give 1.45 g of compound (3a-2) and its oxo/R4 regioisomer as a light brown oil (76% yield). $^1$H-NMR (400 MHz, $CDCl_3$) δ 4.97 (m, 1H), 2.79-0.78 (broad multiplets, mixture of regioisomers).

Inventive Example 3 (prophetic): synthesis of compounds (3a-3) wherein R1 is methyl, R2 is 1-methylethyl, R3 and R3a are H, and R4 is H or methyl

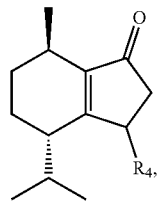

(3a-3)

and their oxo/R4 regioisomers

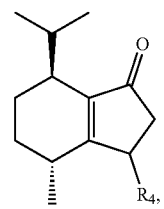

using $P_2O_5/H_3CSO_3H$ mixture: Under a nitrogen atmosphere in a 250 mL round bottom flask equipped with a stir bar, add acrylic acid (compound (2) wherein R4 is H, 116 mmol) or (E)-2-butenoic acid (compound (2) wherein R4 is methyl, 116 mmol), then (3S,6R)-3-(1-methylethyl)-6-methylcyclohexene (compound (1a) wherein R1 is methyl, R2 is 1-methylethyl, R3 and R3a are H, 116 mmol). Cool the reaction mixture to 0° C. Next, add dropwise a $P_2O_5/H_3CSO_3H$ mixture (0.1/1) (55.3 mL, 348 mmol) at 0° C. Warm up the reaction mixture with stirring to ambient temperature, and then continue stirring for 20 hours. Dilute the resulting crude product with 50 mL of water. Add solid $NaHCO_3$ until bubbling subsides and the pH of the reaction mixture reaches pH 8 to pH 9. Separate the aqueous and organic layers in a separatory funnel. Extract the aqueous layer three times with diethyl ether (3×50 mL). Combine the organic layers, and wash with brine (50 mL). Dry over magnesium sulfate and filter. Remove the solvent in vacuo to give a quantity of either compound (3a-3) wherein R4 is H or compound (3a-3) wherein R4 is methyl, and a quantity of its respective oxo/R4 regioisomer. Purify the compound (3a-3) and its oxo/R4 regioisomer by distillation at reduced pressure (1.75 mm Hg) to give purer compound (3a-3) and purer oxo/R4 regioisomer. In compound (3a-3), the stereochemistry of the carbon atom bonded to R1=methyl is (R) and the stereochemistry to the carbon atom bonded to R2=1-methylethyl is (S). Stereochemistry of the carbon atom bonded to R4 is unspecified. In the oxo/R4 regioisomer, the stereochemistry of the carbon atom bonded to R1=1-methylethyl is (S) and the stereochemistry to the carbon atom bonded to R2=methyl is (R). Stereochemistry of the carbon atom bonded to R4 is unspecified.

Inventive Example 4 (prophetic): synthesis of compound (3a-4) wherein R3 is methyl, R3a is ethyl, R1 and R2 are H, and R4 is methyl, and its oxo/R4 regioisomer, using $P_2O_5/H_3CSO_3H$ mixture: Under a nitrogen atmosphere in a 250 mL round bottom flask equipped with a stir bar, add (E)-2-butenoic acid (compound (2) wherein R4 is methyl, 116 mmol), then 4-ethyl-5-methylcyclohexene (compound (1a) wherein R1 and R2 are H, R3 is methyl, and R3a is ethyl, 116 mmol). Cool the reaction mixture to 0° C. Next, add dropwise a $P_2O_5/H_3CSO_3H$ mixture (0.1/1) (55.3 mL, 348 mmol) at 0° C. Warm up the reaction mixture with stirring to ambient temperature, and then continue stirring for 20 hours. Dilute the resulting crude product with 50 mL of water. Add solid NaHCO$_3$ until bubbling subsides and the pH of the reaction mixture reaches pH 8 to pH 9. Separate the aqueous and organic layers in a separatory funnel. Extract the aqueous layer three times with diethyl ether (3×50 mL). Combine the organic layers, and wash with brine (50 mL). Dry over magnesium sulfate and filter. Remove the solvent in vacuo to give a quantity of compound (3a-4) and a quantity of its oxo/R4 regioisomer. Purify the compound (3a-4) and its oxo/R4 regioisomer by distillation at reduced pressure (1.75 mm Hg) to give purer compound (3a-4) and purer oxo/R4 regioisomer with unspecified stereochemistries.

Inventive Example 5 synthesis of compound (3b-1) (compound (3b) wherein R1 to R3 is H and R4 is methyl) using P$_2$O$_5$/H$_3$CSO$_3$H mixture: Under a nitrogen atmosphere in a 250 mL round bottom flask equipped with a stir bar, add (E)-2-butenoic acid (compound (2) wherein R4 is methyl, 5 g, 57.5 millimoles (mmol)), then cyclopentene (compound (1) wherein R1 to R3 is H, 5.6 mL, 63.3 mmol). Cool the reaction mixture to 0° C. Next, add dropwise a P$_2$O$_5$/H$_3$CSO$_3$H mixture (0.1/1) (55.3 mL, 348 mmol) at 0° C. Warm up the reaction mixture with stirring to ambient temperature, and then continue stirring for 20 hours. Dilute the resulting crude product with 50 mL of water. Add solid NaHCO$_3$ until bubbling subsides and the pH of the reaction mixture reaches pH 8 to pH 9. Separate the aqueous and organic layers in a separatory funnel. Extract the aqueous layer three times with diethyl ether (3×50 mL). Combine the organic layers, and wash them with brine (50 mL). Dry over anhydrous magnesium sulfate and filter. Remove the solvent in vacuo to give 5.7 g of compound (3-1) as a dark brown liquid product (72% yield). Characterize compound (3-1) by $^1$H-NMR and GC/MS. $^1$H-NMR (400 MHz, CDCl$_3$) δ 3.01-2.89 (m, 1H), 2.89-2.70 (m, 1H), 2.69-2.48 (m, 1H), 2.46-2.23 (m, 6H), 2.18-1.34 (m, 4H), 1.17 (d, 3H).

Inventive Example 6 synthesis of compound (3c-1) using P2O5/H3CSO3H mixture: compound (3c) wherein R1 to R3b is H and R4 is methyl. In a round bottom flask equipped with a stir bar, under a nitrogen atmosphere add (E)-2-butenoic acid (compound (2) wherein R4 is methyl, 0.40 g, 4.64 mmol), then cycloheptene (compound (1c) wherein R1 to R3b is H, 0.542 mL, 4.64 mmol). Next, sulfolane is added (2.2 mL). Cool the reaction mixture to 0° C. Next, add dropwise a 0.1/1 (wt/wt) P$_2$O$_5$/CH$_3$SO$_3$H mixture (2.21 mL, 13.94 mmol) at 0° C. Warm up the reaction to ambient temperature and stirred for 18 hours. Dilute the crude product into 20 mL of water and 20 mL of diethyl ether. Add solid NaHCO3 until bubbling subsides. Decant the liquid layer, and separate the aqueous and organic layers. Extract the aqueous layer twice with diethyl ether (2×5 mL). Combine the organic layers, and wash them with saturated NaHCO$_3$ (10 mL), then brine (15 mL). Dry over magnesium sulfate, and filter. Remove the solvent in vacuo to give a light brown oil product (0.64 g, 84% yield). Characterize compound (3c-1) by $^1$HNMR, $^{13}$CNMR and GC/MS. $^1$H-NMR (400 MHz, CDCl$_3$) 2.69-1.17 (broad multiplets), 1.14 (d, 3H).

Inventive Example 7: synthesis of compound (3a-2) and its oxo/R4 regioisomer using P$_2$O$_5$/H$_3$CSO$_3$H mixture: compound (3a) wherein R1, R2, and R3a are H and R3 and R4 are methyl, and its oxo/R4 regioisomer. In a fume hood under a nitrogen atmosphere, in a round bottom flask equipped with a stir bar, add (E)-2-butenoic acid (compound (2) wherein R4 is methyl, 1 g, 11.6 mmol), then add 4-methyl-1-cyclohexene (compound (1) wherein R3 is methyl, 1.4 mL, 11.6 mmol). Next, add Sulfolane (6 mL). Cool the reaction mixture to −10° C. Next, add dropwise P$_2$O$_5$/H$_3$CSO$_3$H mixture (0.1:1) (5.53 mL, 34.8 mmol) at −10° C. Keep the reaction mixture at −10° C. for 1 hour. Warm up the reaction mixture with stirring to room temperature, and then continue stirring for 20 hours. Dilute the mixture into 50 mL of water and 50 mL of diethyl ether. Add solid NaHCO$_3$ until bubbling subsides. Decant the liquid layer. Separate the aqueous and organic layers. Extract the aqueous layer twice with diethyl ether (2×15 mL). Combine the organic layers, and wash with saturated NaHCO$_3$ (20 mL), then brine (30 mL). Dry over magnesium sulfate and filter. Remove the solvent in vacuo to give 1.5 g of compound (3-2) and its oxo/R4 regioisomer as a light brown oil (79% yield). 1H-NMR (400 MHz, CDCl$_3$) δ 4.97 (m, 1H), 2.79-0.78 (broad multiplets, mixture of regioisomers).

As discussed earlier, Conia et al., Rand and Dolinski, and others report that using PPA or a P$_2$O$_5$/PPA mixture to catalyze a reaction of cycloheptene, cyclohexene, or cyclopentene with an alpha,beta-unsaturated carboxylic acid, such as acrylic acid or crotonic acid, gives a reaction mixture that contains an ester by-product (e.g., cycloheptyl crotonate, cyclohexyl crotonate, or cyclopentyl crotonate, respectively). We found that using a sulfonic acid reagent (P$_2$O$_5$/H$_3$CSO$_3$H reagent) to catalyze a reaction of cycloheptene, cyclohexene, or cyclopentene with an alpha,beta-unsaturated carboxylic acid such as acrylic acid or crotonic acid gives a reaction mixture that does not contain an ester by-product (e.g., the reaction does not yield cycloheptyl crotonate, cyclohexyl crotonate, or cyclopentyl crotonate, respectively). We base this observation on analysis of at least one of the reaction mixtures by gas chromatography-mass spectrometry (GC-MS), which fails to show any ester by-product. We also base this observation on seeing that the reaction of cycloheptene, cyclohexene, or cyclopentene with an alpha,beta-unsaturated carboxylic acid, such as acrylic acid or crotonic acid, in the presence of the P$_2$O$_5$/H$_3$CSO$_3$H reagent goes much faster than a reaction of cycloheptyl crotonate, cyclohexyl crotonate, or cyclopentyl crotonate, respectively, in the presence of the P$_2$O$_5$/H$_3$CSO$_3$H reagent. Without wishing to be bound by theory, we believe that the P$_2$O$_5$/H$_3$CSO$_3$H reagent reacts with the alpha,beta-unsaturated carboxylic acid (e.g., crotonic acid) to give in situ a mixed anhydride of general formula R$_4$CH=CHC(=O)—O—SO$_2$—CH$_3$, which generates in situ an acylium ion (i.e., acyl carbonium ion) of formula R$_4$CH=CHC$^+$(=O), which rapidly undergoes a Friedel-Crafts acylation of cycloalkene to give in situ a ketone of formula R$^a$—C(=O)—R$^e$, wherein R$^a$ is R4CH=CH— and R$^e$ is cycloalken-1-yl, which ketone undergoes cyclization reaction to give the corresponding cyclopentenone. For example, when the cycloalkene is cyclohexene and the alpha,beta-unsaturated carboxylic acid is crotonic acid, we believe that the P$_2$O$_5$/H$_3$CSO$_3$H reagent reacts with the crotonic acid to give in situ a mixed anhydride of general formula H$_3$CCH=CHC(=O)—O—SO$_2$—CH$_3$, which generates in situ an acylium ion (i.e., acyl carbonium ion) of formula H$_3$CCH=CHC$^+$(=O), which rapidly undergoes a Friedel-Crafts acylation of cycloalkene to give in situ a ketone of formula R$^a$—C(=O)—R$^e$, wherein R$^a$ is H$_3$CCH=CH— and R$^e$ is cyclohexen-1-yl, which ketone undergoes cyclization reaction to give the corresponding cyclopentenone that is 2,3,4,5,6,7-hexahydro-3-methyl-1H-inden-1-one (i.e., 7-methyl-bicyclo[4.3.0]-7-nonen-9-one). Therefore, using the P$_2$O$_5$/H$_3$CSO$_3$H reagent in reaction of a cycloalkene such as cycloheptene, cyclohexene, or cyclopentene with an alpha,beta-unsaturated carboxylic acid such as acrylic acid or crotonic acid does not inherently make the ester by-product (e.g., cycloheptyl crotonate, cyclohexyl crotonate, or cyclopentyl crotonate, respectively) reported by Conia et al., Rand and Dolinski, and others using PPA or P₂O₅/PPA mixture.

The invention claimed is:

1. A method of synthesizing a cyclic organic compound, the method comprising (A) contacting a compound of formula (1) ("compound (1)"): R1(H)C=C(H)R2 (1), wherein each R1 and R2 is independently H or $(C_1-C_6)$ alkyl or substituted $(C_1-C_6)$ alkyl, or the R1 and R2 are bonded together as R—R— to form a $(C_1-C_4)$ alkylene or substituted alkylene, with a compound of formula (2) ("compound (2)"):

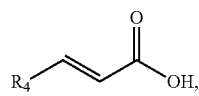

(2)

wherein R4 is H or (C1-C4)alkyl, in the presence of an effective amount of a sulfonic acid reagent and under reaction conditions sufficient to make a compound of formula (3) ("compound (3)"):

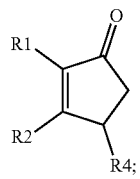

(3)

and/or its oxo/R4 regioisomer, wherein R1, R2, and R4 are as defined above.

2. The method of claim 1 wherein the sulfonic acid reagent comprises a $(C_1-C_6)$alkylsulfonic acid.
3. The method of claim 1 wherein the sulfonic acid reagent comprises a mixture of $P_2O_5$ and a $(C_1-C_6)$alkylsulfonic acid, or a reaction product thereof.
4. The method of claim 1 wherein the sulfonic acid reagent comprises a mixture of $P_2O_5$ and methanesulfonic acid, or a reaction product thereof.
5. The method of claim 1 wherein the sulfonic acid reagent comprises a mixture of 0.1 weight parts $P_2O_5$ and 1 weight part methanesulfonic acid, or a reaction product thereof.
6. The method of claim 1 wherein the sulfonic acid reagent consists essentially of methanesulfonic acid.
7. The method of claim 1 comprising (A) contacting a compound of formula (1a) ("compound (1a)"):

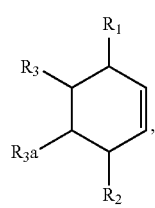

(1a)

wherein R1, R2, R3, and R3a are independently H or $(C_1-C_4)$alkyl, or any two adjacent R1 to R3a groups are bonded together to form a $(C_1-C_4)$alkylene and the remaining two R1 to R3a groups independently are H or $(C_1-C_4)$ alkyl, with a compound of formula (2) ("compound (2)"):

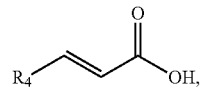

(2)

wherein R4 is H or $(C_1-C_4)$alkyl, in the presence of an effective amount of a sulfonic acid reagent and under reaction conditions sufficient to make a compound of formula (3a) ("compound (3a)"):

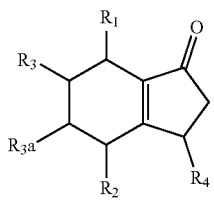

(3a)

and/or its oxo/R4 regioisomer; wherein R1 to R4 are as defined above.

8. The method of claim 1 comprising (A) contacting a compound of formula (1b) ("compound (1b)"):

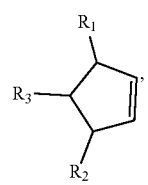

(1b)

wherein R1, R2, and R3 are independently H or (C1-C4) alkyl, or any two adjacent R1 to R3 groups are bonded together to form a $(C_1-C_4)$alkylene and the remaining one of the R1 to R3 groups is H or $(C_1-C_4)$alkyl, with a compound of formula (2) ("compound (2)"):

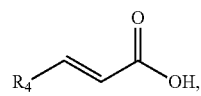

(2)

wherein R4 is H or (C1-C4)alkyl, or any two adjacent R1 to R3 groups are bonded together to form a $(C_1-C_4)$alkylene and the remaining R1 to R3 group independently is H or $(C_1-C_4)$alkyl, in the presence of an effective amount of a sulfonic acid reagent and under reaction conditions sufficient to make a compound of formula (3b) ("compound (3b)"):

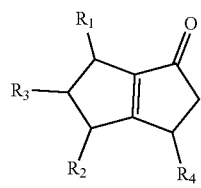
(3b)

and/or its oxo/R4 regioisomer; wherein R1 to R4 are as defined above.

9. The method of claim 1 comprising (A) contacting a compound of formula (1c) ("compound (1c)"):

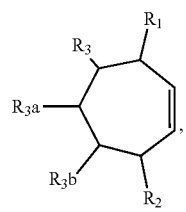
(1c)

wherein R1, R2, R3, R3a, and R3b are independently H or (C1-C4)alkyl, or any two adjacent R1 to R3b groups are bonded together to form a $(C_1-C_4)$alkylene and the remaining three R1 to R3b groups independently are H or $(C_1-C_4)$ alkyl, with a compound of formula (2) ("compound (2)"):

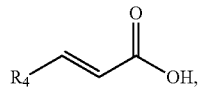
(2)

wherein R4 is H or (C1-C4)alkyl, in the presence of an effective amount of a sulfonic acid reagent and under reaction conditions sufficient to make a compound of formula (3c) ("compound (3c)"):

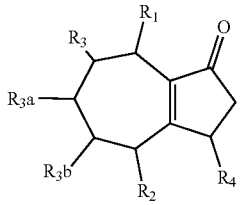
(3c)

and/or its oxo/R4 regioisomer; wherein R1 to R4 are as defined above.

* * * * *